(12) United States Patent
Racchini et al.

(10) Patent No.: US 7,258,673 B2
(45) Date of Patent: *Aug. 21, 2007

(54) DEVICES, SYSTEMS AND METHODS FOR EXTRACTING BODILY FLUID AND MONITORING AN ANALYTE THEREIN

(75) Inventors: Joel Racchini, Edina, MN (US); Michael Hilgers, Lake Elmo, MN (US); Phil Stout, Roseville, MN (US); Thomas Rademacher, St. Paul, MN (US); Joel Mechelke, Stillwater, MN (US); Cass A. Hanson, St. Paul, MN (US)

(73) Assignee: Lifescan, Inc, Milpitas, CA (US)

( * ) Notice: Subject to any disclaimer, the term of this patent is extended or adjusted under 35 U.S.C. 154(b) by 586 days.

This patent is subject to a terminal disclaimer.

(21) Appl. No.: 10/653,023

(22) Filed: Aug. 28, 2003

(65) Prior Publication Data

US 2004/0249253 A1 Dec. 9, 2004

Related U.S. Application Data

(60) Provisional application No. 60/476,733, filed on Jun. 6, 2003.

(51) Int. Cl.
*A61B 5/00* (2006.01)
*A61B 17/14* (2006.01)
*A61B 17/32* (2006.01)

(52) U.S. Cl. ........................ 600/583; 606/181

(58) Field of Classification Search ................ 600/576, 600/578, 583, 584, 573; 606/181–183
See application file for complete search history.

(56) References Cited

U.S. PATENT DOCUMENTS 5,002,054 A    3/1991  Ash et al.
5,139,023 A    8/1992  Stanley et al.
5,165,418 A   11/1992  Tankovich (Continued)

FOREIGN PATENT DOCUMENTS

| EP | 1260815 A2 | 11/2002 |
|----|------------|---------|
| GB | 2375053 A | 11/2002 |
| WO | WO97/07734 A1 | 3/1997 |
| WO | WO 01/47408 A1 | 7/2001 |
| WO | WO 02/49507 A1 | 6/2002 |

OTHER PUBLICATIONS

European Search Report (Corrected Version), European Patent Office, dated Nov. 9, 2004, EP 04253352.1.

(Continued)

*Primary Examiner*—Max F. Hindenburg
*Assistant Examiner*—Michael Apanius

(57) ABSTRACT

An interstitial fluid (ISF) extraction device includes a penetration member configured for penetrating a target site of a user's skin layer and, subsequently, residing in the user's skin layer and extracting an ISF sample therefrom and at least three concentrically-arranged pressure rings, each adapted for applying pressure to the user's skin layer in the vicinity of the target site while the penetration member is residing in the user's skin layer. In addition, the ISF extraction device is configured such that (i) the pressure rings apply pressure in an oscillating manner with asymmetric deployment and retraction cycles and (ii) only one of the at least three concentrically-arranged pressure rings is deployed at a time, thereby mitigating an ISF glucose lag of the ISF sample extracted by the penetration member.

6 Claims, 9 Drawing Sheets

U.S. PATENT DOCUMENTS

| | | | |
|---|---|---|---|
| 5,174,291 A | 12/1992 | Schoonen et al. | |
| 5,231,975 A | 8/1993 | Bommannan et al. | |
| 5,279,543 A | 1/1994 | Glikfeld et al. | 604/20 |
| 5,362,307 A | 11/1994 | Guy et al. | 604/20 |
| 5,458,140 A | 10/1995 | Eppstein et al. | |
| 5,582,184 A | 12/1996 | Erickson et al. | |
| 5,706,806 A | 1/1998 | Kissinger | |
| 5,730,714 A | 3/1998 | Guy et al. | 604/20 |
| 5,735,273 A | 4/1998 | Kurnik et al. | 128/635 |
| 5,746,217 A | 5/1998 | Erickson et al. | |
| 5,771,890 A | 6/1998 | Tamada | 128/635 |
| 5,820,570 A | 10/1998 | Erickson et al. | |
| 5,827,183 A | 10/1998 | Kurnik et al. | 600/345 |
| 5,857,983 A * | 1/1999 | Douglas et al. | 600/583 |
| 5,879,367 A | 3/1999 | Latterell et al. | |
| 5,951,493 A * | 9/1999 | Douglas et al. | 600/583 |
| 5,954,685 A | 9/1999 | Tierney | 604/20 |
| 5,956,501 A | 9/1999 | Brown | |
| 6,022,316 A | 2/2000 | Eppstein et al. | |
| 6,023,629 A | 2/2000 | Tamada | 600/347 |
| 6,040,194 A | 3/2000 | Chick et al. | |
| 6,080,116 A | 6/2000 | Erickson et al. | |
| 6,141,573 A | 10/2000 | Kurnik et al. | 600/345 |
| 6,144,869 A | 11/2000 | Berner et al. | 600/347 |
| 6,155,992 A | 12/2000 | Henning et al. | |
| 6,180,416 B1 | 1/2001 | Kurnik et al. | 436/518 |
| 6,201,979 B1 | 3/2001 | Kurnik et al. | 600/345 |
| 6,203,504 B1 | 3/2001 | Latterell et al. | |
| 6,232,130 B1 | 5/2001 | Wolf | |
| 6,233,471 B1 | 5/2001 | Berner et al. | |
| 6,234,990 B1 | 5/2001 | Kost et al. | |
| 6,240,306 B1 | 5/2001 | Rohrscheib et al. | |
| 6,251,083 B1 | 6/2001 | Roe et al. | |
| 6,272,364 B1 | 8/2001 | Kurnik | |
| 6,275,717 B1 | 8/2001 | Gross et al. | |
| 6,298,254 B2 | 10/2001 | Tamada | 600/347 |
| 6,299,578 B1 | 10/2001 | Kurnik et al. | 600/309 |
| 6,309,351 B1 | 10/2001 | Kurnik et al. | 600/309 |
| 6,319,210 B1 | 11/2001 | Graga et al. | |
| 6,326,160 B1 | 12/2001 | Dunn et al. | 435/14 |
| 6,329,161 B1 | 12/2001 | Heller et al. | |
| 6,332,871 B1 | 12/2001 | Douglas et al. | |
| 6,341,232 B1 | 1/2002 | Conn et al. | 604/20 |
| 6,356,776 B1 | 3/2002 | Berner et al. | 600/347 |
| 6,370,410 B2 | 4/2002 | Kurnik et al. | 600/345 |
| 6,393,318 B1 | 5/2002 | Conn et al. | 604/20 |
| 6,424,847 B1 | 7/2002 | Mastrototaro et al. | |
| 6,438,414 B1 | 8/2002 | Conn et al. | 604/20 |
| 6,464,699 B1 | 10/2002 | Swanson | 606/41 |
| 6,468,229 B1 | 10/2002 | Grace et al. | |
| 6,514,718 B2 | 2/2003 | Heller et al. | |
| 6,529,755 B2 | 3/2003 | Kurnik et al. | 600/345 |
| 6,542,765 B1 | 4/2003 | Guy et al. | 600/345 |
| 6,546,269 B1 | 4/2003 | Kurnik | 600/345 |
| 6,558,321 B1 | 5/2003 | Burd et al. | |
| 6,561,978 B1 | 5/2003 | Conn et al. | 600/309 |
| 6,579,690 B1 | 6/2003 | Bonnecaze et al. | |
| 6,587,705 B1 | 7/2003 | Kim et al. | 600/347 |
| 6,591,125 B1 | 7/2003 | Buse et al. | |
| 6,594,514 B2 | 7/2003 | Berner et al. | 600/347 |
| 6,595,919 B2 | 7/2003 | Berner et al. | 600/365 |
| 6,653,091 B1 | 11/2003 | Dunn et al. | 435/14 |
| 6,687,522 B2 | 2/2004 | Tamada | 600/347 |
| 6,702,857 B2 | 3/2004 | Shults et al. | |
| 6,706,000 B2 * | 3/2004 | Perez et al. | 600/583 |
| 6,706,159 B2 * | 3/2004 | Moerman et al. | 204/403.03 |
| 6,714,815 B2 | 3/2004 | Guy et al. | 604/20 |
| 6,718,189 B2 | 4/2004 | Rohrscheib et al. | |
| 6,736,777 B2 | 5/2004 | Kim et al. | 600/365 |
| 2002/0019022 A1 | 2/2002 | Dunn et al. | |
| 2002/0022789 A1 | 2/2002 | Roe | |
| 2002/0082522 A1 | 6/2002 | Radwanski | |
| 2002/0188223 A1* | 12/2002 | Perez et al. | 600/573 |
| 2003/0018300 A1 | 1/2003 | Duchon et al. | |
| 2003/0055326 A1 | 3/2003 | Sohrab | |
| 2003/0060784 A1 | 3/2003 | Hilgers et al. | |
| 2003/0073931 A1 | 4/2003 | Boecker et al. | |
| 2003/0212379 A1* | 11/2003 | Bylund et al. | 604/504 |
| 2006/0184189 A1* | 8/2006 | Olson et al. | 606/181 |

OTHER PUBLICATIONS

Ben Feldman, et al. "A Continuous Glucose Sensor Based on Wired Enzyme Technology—Results from a 3-day Trial in Patients with type 1 Diabetes", Diabetes Technology & Therapeutics, vol. 5, No. 5, 2003.

Satish K. Garg, et al. "Improved Glucose Excursions Using an Implantable Real-Time Continuous Glucose Sensor in Adults with Type 1 Diabetes", Diabetes Care, vol. 27, No. 3, Mar. 2004.

Karsten Jungheim, et al. "Glucose Monitoring at the Arm", Diabetes Care, vol. 25, No. 6, Jun. 2002.

Schmidtke et al., "Measurement and modeling of the transient difference between blood and subcutaneous glucose concentrations in the rat after injection of insulin". Proceedings of the National Academy of Sciences of the United States of America, vol. 95, Jan. 1998, pp. 294-299, XP00120307; p. 296, col. 1-p. 298, col. 1.

European Patent Search Report for Application 04255207.5 dated Nov. 17, 2004.

Patent Cooperation Treaty International Search Report,European Patent Office, for Application PCT/US2004,018144, dated Oct. 27, 2004.

Chase, HP., et al., "Use of the GlucoWatch® Biographer in Children with Type 1 Diabetes", Pediatrics, 111(4):790-794 (2003).

Eastman, RC., et al., "Use of the GlucoWatch® Biographer in Children and Adolescents with Diabetes", Pediatric Diabetes, 3:127-134 (2002).

Erickson, D., "Skinside Out", Scientific American, November pp. 128&130 (1991).

Garg, SK., et al., "Correlation of Fingerstick Blood Glucose Measurements with GlucoWatch™ Biographer Glucose Results in Young Subjects with Type 1 Diabetes", Diabetes Care, 22(10):1708-1714 (1999).

Glikfeld, P., et al., "Noninvasive Sampling of Biological Fluids by Iontophoresis", Plenum Publishing Corporation, 6(11):988-990 (1989).

Kurnik, R., et al., "Application of the Mixtures of Experts Algorithm for Signal Processing in a Non-invasive Glucose Monitoring System", Sensors and Actuators., 60(1):19-26 (1999).

Kurnik, R., et al., "Design and Simulation of a Reverse Iontophoretic Glucose Monitoring Device", J Electrochem Soc., 145(12):4119-4125 (1998).

Pitzer, KR., et al., "Detection of Hypoglycemia with the GlucoWatch® Biographer", Diabetes Care, 24(5):881-885 (2001).

Potts, R., et al., "Glucose Monitoring by Reverse Iontophoresis", Diabetes Metab Res Rev., 18(suppl 1):s49-s53 (2002).

Rao, G., et al., Iontophoretic and Noninvasive Glucose Monitoring, Proceed Intern. Symp. Control Rel. Bioact. Mater., 21:13-14 (1994).

Tamada, J., et al., "Measurements of Glucose in Diabetic Subjects Using Non-invasive Transdermal Extraction", Nature Medicine, 1(11):1198-1201 (1995).

Tamada, JA., et al., "Keeping Watch on Glucose", IEEE Spectrum, Apr.: pp. 52-57 (2002).

Tamada, JA., et al., "Noninvasive Glucose Monitoring: Comprehensive Clinical Results", JAMA, 282(19):1839-1844 (1999).

Tierney, M., "Transdermal Glucose Monitoring Opens a New Age of Diabetes Management", IVD Technology, 9(4):51-56 (2003).

Tierney, M., et al., "A Non-invasive Glucose Monitor: The GlucoWatch® Biographer", *The Biochemist,* 23(6):17-19 (2001).

Tierney, M., et al., "Clinical Evaluation of the GlucoWatch® Biographer: A Continual, Non-invasive Glucose Monitor for Patients with Diabetes", *Biosensors & Bioelectronics,* 16:621-629 (2001).

Tierney, M., et al., "Effect of Acetaminophen on the Accuracy of Glucose Measurements Obtained with the GlucoWatch Biographer", Diabetes Technology & Therapeutics, 2(2):199-207 (2000).

Tierney, M., et al., "Electroanalysis of Glucose in Transcutaneously Extracted Samples", Electroanalysis, 12(9):666-671 (2000).

Tierney, M., et al., "The GlucoWatch® Biographer: A Frequent, Automatic and Noninvasive Glucose Monitor", Annals Med, 32(9):632-641 (2000).

Uhegbu, C., et al., "Management of Interferences in a Transdermal, Noninvasive Glucose Monitoring Device", Clinical Chemistry, 45(9):1679-1681 (1999).

* cited by examiner

DEVICES, SYSTEMS AND METHODS FOR EXTRACTING BODILY FLUID AND MONITORING AN ANALYTE THEREIN

This application claims the benefit of U.S. Provisional Application No. 60/476,733 filed Jun. 6, 2003, which is fully incorporated herein by reference.

BACKGROUND OF INVENTION

1. Field of the Invention

The present invention relates, in general, to medical devices and their associated methods and, in particular, to devices, systems and methods for extracting bodily fluid and monitoring an analyte therein.

2. Description of the Related Art

In recent years, efforts in medical devices for monitoring analytes (e.g., glucose) in bodily fluids (e.g., blood and interstitial fluid) have been directed toward developing devices and methods with reduced user discomfort and/or pain, simplifying monitoring methods and developing devices and methods that allow continuous or semi-continuous monitoring. Simplification of monitoring methods enables users to self-monitor such analytes at home or in other locations without the help of health care professionals. A reduction in a user's discomfort and/or pain is particularly important in devices and methods designed for home use in order to encourage frequent and regular use. It is thought that if a blood glucose monitoring device and associated method are relatively painless, users will monitor their blood glucose levels more frequently and regularly than otherwise.

In the context of blood glucose monitoring, continuous or semi-continuous monitoring devices and methods are advantageous in that they provide enhanced insight into blood glucose concentration trends, the effect of food and medication on blood glucose concentration and a user's overall glycemic control. In practice, however, continuous and semi-continuous monitoring devices can have drawbacks. For example, during extraction of an interstitial fluid (ISF) sample from a target site (e.g., a target site in a user's skin layer), ISF flow rate can decay over time. Furthermore, after several hours of continuous ISF extraction, a user's pain and/or discomfort can increase significantly and persistent blemishes can be created at the target site.

Still needed in the field, therefore, is a device and associated method for the monitoring of an analyte (e.g., glucose) in a bodily fluid (such as ISF) that is simple to employ, creates relatively little discomfort and/or pain in a user, and facilitates continuous or semi-continuous monitoring without unduly increasing a user's pain or creating persistent blemishes.

SUMMARY OF INVENTION

Systems for the extraction of a bodily fluid sample and monitoring of an analyte therein according to embodiments of the present invention are simple to employ, create relatively little pain and/or discomfort in a user, and facilitate continuous and semi-continuous monitoring without unduly increasing a user's pain or creating persistent blemishes. In addition, ISF extraction devices according to embodiments of the present invention also create relatively little pain and/or discomfort in a user and facilitate continuous and semi-continuous monitoring without unduly increasing a user's pain or creating persistent blemishes. Moreover, methods according to the present invention facilitate continuous or semi-continuous monitoring without unduly increasing a user's pain or creating persistent blemishes.

A system for extracting a bodily fluid sample and monitoring an analyte therein according to an exemplary embodiment of the present invention includes a disposable cartridge and a local controller module. The disposable cartridge includes a sampling module adapted to extract a bodily fluid sample (e.g., an ISF sample) from a body and an analysis module adapted to measure an analyte (for example, glucose) in the bodily fluid sample. In addition, the local controller module is in electronic communication with the disposable cartridge and is adapted to receive and store measurement data (e.g., a current signal) from the analysis module.

The sampling module of systems according to embodiments of the present invention can optionally includes a penetration member configured for penetrating a target site of a user's skin layer and, subsequently, residing in the user's skin layer and extracting an ISF sample therefrom. The sampling module also optionally includes at least one pressure ring adapted for applying pressure to the user's skin layer in the vicinity of the target site while the penetration member is residing in the user's skin layer. In addition, if desired, the sampling module can be configured such that the pressure ring(s) is capable of applying pressure to the user's skin layer in an oscillating manner whereby an ISF glucose lag of the ISF sample extracted by the penetration member is mitigated.

The disposable nature of the disposable cartridge renders systems according to the present invention simple to employ. In addition, when a pressure ring is operated in an oscillating manner according to the present invention, continuous and semi-continuous monitoring is facilitated while simultaneously minimizing a user's pain and the creation of persistent blemishes.

An interstitial fluid (ISF) extraction device according to an embodiment of the present invention includes a penetration member (e.g., a thin-walled needle with a bore) configured for penetrating a target site of a user's skin layer and, subsequently, residing in a user's skin layer and extracting an ISF sample therefrom. The ISF extraction device also includes at least one pressure ring (e.g., three concentrically arranged pressure rings) adapted for applying pressure to the user's skin layer in the vicinity of the target site while the penetration member is residing in the user's skin layer. The ISF extraction device is configured such that the pressure ring(s) is capable of applying the pressure in an oscillating manner whereby an ISF glucose lag of the ISF sample extracted by the penetration member is mitigated.

Since the penetration member of ISF extraction devices according to embodiments of the present invention can reside in a user's skin layer during extraction of an ISF sample, the ISF extraction devices are simple to employ. In addition, since the ISF extraction device is configured to apply pressure in an oscillating manner, continuous and semi-continuous monitoring is facilitated while minimizing a user's pain and the creation of persistent blemishes. Application of pressure in an oscillating manner by the pressure ring(s) can also optimize blood flow to the vicinity of the target site such that ISF glucose lag is minimized.

A method for extracting interstitial fluid (ISF) according to an embodiment of the present invention includes providing an ISF fluid extraction device with a penetration member and at least one pressure ring. Next, a user's skin layer is contacted by the pressure ring and penetrated by the pen etration member. An ISF sample is then extracted from the user's skin layer via the penetration member while applying pressure to the user's skin layer in an oscillating manner using the pressure ring(s). The oscillating manner, by which the pressure is applied, serves to mitigate an ISF glucose lag of the ISF sample extracted by the penetration member and/or to facilitate continuous or semi-continuous extraction of an ISF sample for an extended time period (e.g., an extended time period in the range of one hour to 24 hours).

BRIEF DESCRIPTION OF DRAWINGS

A better understanding of the features and advantages of the present invention will be obtained by reference to the following detailed description that sets forth illustrative embodiments, in which principles of the invention are utilized, and the accompanying drawings of which.

DETAILED DESCRIPTION OF THE INVENTION

Figure 1:
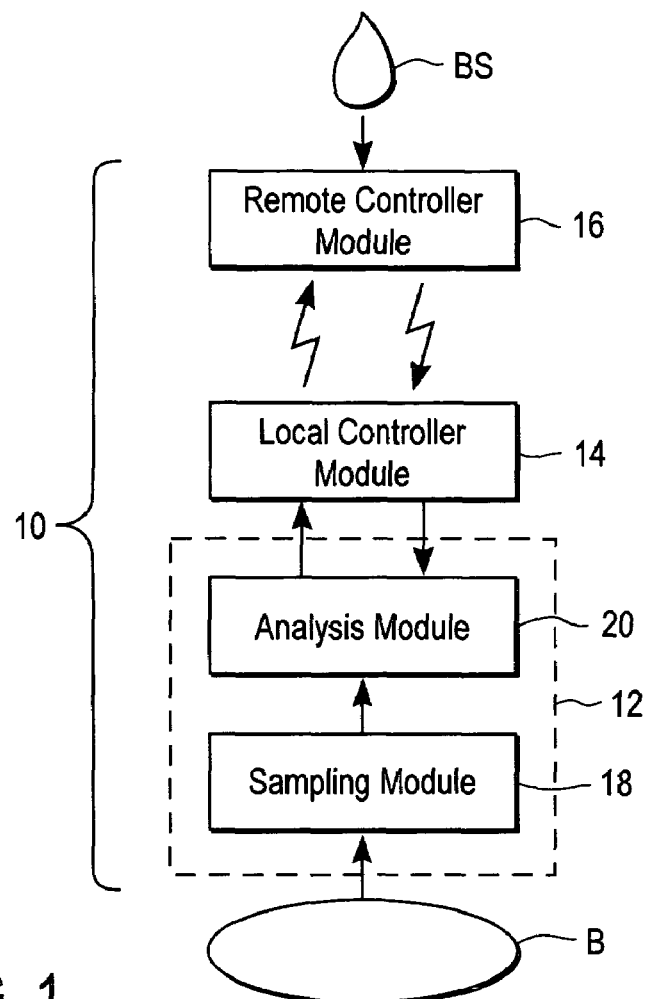
FIG. 1 is a simplified block diagram depicting a system for extracting a bodily fluid sample and monitoring an analyte therein according to an exemplary embodiment of the present invention.

A system 10 for extracting a bodily fluid sample (e.g., an ISF sample) and monitoring an analyte (for example, glucose) therein according to an exemplary embodiment of the present invention includes a disposable cartridge 12 (encompassed within the dashed box), a local controller module 14, and a remote controller module 16, as illustrated in FIG. 1.

In system 10, disposable cartridge 12 includes a sampling module 18 for extracting the bodily fluid sample (namely, an ISF sample) from a body (B, for example a user's skin layer) and an analysis module 20 for measuring an analyte (i.e., glucose) in the bodily fluid. Sampling module 18 and analysis module 20 can be any suitable sampling and analysis modules known to those of skill in the art. Examples of suitable sampling and analysis modules are described in International Application PCT/GB01/05634 (International Publication Number WO 02/49507 A1), which is hereby fully incorporated herein by reference. However, in system 10, sampling module 18 and analysis module 20 are both configured to be disposable since they are components of disposable cartridge 12.

Figure 2:
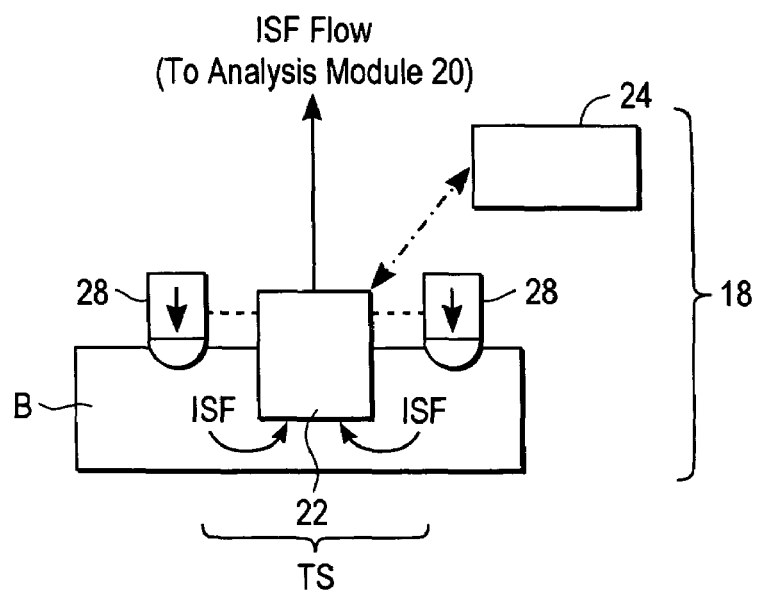
FIG. 2 is a simplified schematic diagram of an ISF sampling module according to an exemplary embodiment of the present invention being applied to a user's skin layer, with the dashed arrow indicating a mechanical interaction and the solid arrows indicating ISF flow or, when associated with element 28, the application of pressure.

As depicted in FIG. 2, the particular sampling module 18 of system 10 is, however, an ISF sampling module that includes a penetration member 22 for penetrating a target site (TS) of body B and extracting an ISF sample, a launching mechanism 24 and at least one pressure ring 28. ISF sampling module 18 is adapted to provide a continuous or semi-continuous flow of ISF to analysis module 20 for the monitoring (e.g., concentration measurement) of an analyte (such as glucose) in the ISF sample.

During use of system 10, penetration member 22 is inserted into the target site (i.e., penetrates the target site) by operation of launching mechanism 24. For the extraction of an ISF sample from a user's skin layer, penetration member 22 can be inserted to a maximum insertion depth in the range of, for example, 1.5 mm to 3 mm. In addition, penetration member 22 can be configured to optimize extraction of an ISF sample in a continuous or semi-continuous manner. In this regard, penetration member 22 can include, for example, a 25 gauge, thin-wall stainless steel needle (not shown in FIG. 1 or 2) with a bent tip, wherein a fulcrum for the tip bend is disposed between the needle's tip and the needle's heel. Suitable needles for use in penetration members according to the present invention are described in U.S. Patent Application Publication US 2003/0060784 A1 (application Ser. No. 10/185,605).

Launching mechanism 24 can optionally include a hub (not shown in FIG. 1 or 2) surrounding penetration member 22. Such a hub is configured to control the insertion depth of penetration member 22 into the target site. Insertion depth control can be beneficial during the extraction of an ISF sample by preventing inadvertent lancing of blood capillaries, which are located relatively deep in a user's skin layer, and thereby eliminating a resultant fouling of an extracted ISF sample, clogging of the penetration member or clogging of an analysis module by blood. Controlling insertion depth can also serve to minimize pain and/or discomfort experienced by a user during use of system 10.

Although FIG. 2 depicts launching mechanism 24 as being included in sampling module 18, launching mechanism 24 can optionally be included in disposable cartridge 12 or in local controller module 14 of system 10. Furthermore, to simplify employment of system 10 by a user, sampling module 18 can be formed as an integral part of the analysis module 20.

In order to facilitate the extraction of a bodily fluid (e.g., ISF) from the target site, penetration member 22 can be arranged concentrically within at least one pressure ring 28. Pressure ring(s) 28 can be of any suitable shape, including but not limited to, annular. In addition, pressure ring(s) 28 can be configured to apply an oscillating mechanical force (i.e., pressure) in the vicinity of the target site while the penetration member is residing in the user's skin layer. Such oscillation can be achieved through the use of a biasing element (not shown in FIG. 1 or 2), such as a spring or a retention block. The structure and function of a pressure ring(s) in sampling modules (and ISF extraction devices) according to the present invention are described in more detail below with respect to FIGS. 9-12.

During use of system 10, pressure ring 28 is applied in the vicinity of the target site TS, prior to penetration of the target site by penetration member 22, in order to tension the user's skin layer. Such tension serves to stabilize the user's skin layer and prevent tenting thereof during penetration by the penetrating member. Alternatively, stabilization of the user's skin layer prior to penetration by the penetrating member can be achieved by a penetration depth control element (not shown) included in sampling module 18. Such a penetration depth control element rests or "floats" on the surface of the user's skin layer, and acts as a limiter for controlling penetration depth (also referred to as insertion depth). Examples of penetration depth control elements and their use are described in U.S. patent application Ser. No. 10/690,083, which is hereby fully incorporated herein by reference. If desired, the penetration member can be launched coincidentally with application of the pressure ring(s) to the user's skin layer, thereby enabling a simplification of the launching mechanism.

Once penetration member 22 has been launched and has penetrated the target site TS, a needle (not shown in FIG. 1 or 2) of penetration member 22 will reside, for example, at an insertion depth in the range of about 1.5 mm to 3 mm below the surface of the user's skin layer at the target site. The pressure ring(s) 28 applies/apply a force on the user's skin layer (indicated by the downward pointing arrows of FIG. 2) that pressurizes ISF in the vicinity of the target site. A sub-dermal pressure gradient induced by the pressure ring(s) 28 results/result in flow of ISF up the needle and through the sampling module to the analysis module (as indicated by the curved and upward pointing arrows of FIG. 2).

ISF flow through a penetration member's needle is subject to potential decay over time due to depletion of ISF near the target site and due to relaxation of the user's skin layer under the pressure ring(s) 28. However, in systems according to the present invention, pressure ring(s) 28 can be applied to the user's skin layer in an oscillating manner (e.g., with a predetermined pressure ring(s) cycling routine or with a pressure ring cycling routine that is controlled via ISF flow rate measurement and feedback) while the penetration member is residing in the user's skin layer in order to minimize ISF flow decay. In addition, during application of pressure in an oscillating manner, there can be time periods during which the pressure applied by the pressure ring(s) is varied or the local pressure gradient is removed and the net outflow of ISF from the user's skin layer is eliminated.

Furthermore, alternating the application of a plurality of pressure rings to the user's skin layer in the vicinity of the target site can serve to control the flow of ISF through the sampling and analysis modules and limit the time that any given portion of the user's skin layer is under pressure. By allowing a user's skin layer to recover, the application of pressure in an oscillating manner also reduces blemishes on the user's skin and a user's pain and/or discomfort. An additional beneficial effect of applying pressure ring(s) 28 in an oscillating manner is that ISF glucose lag (i.e., the difference between glucose concentration in a user's ISF and glucose concentration in a user's blood) is reduced.

Once apprised of the present disclosure, one skilled in the art can devise a variety of pressure ring cycling routines that serve to reduce ISF glucose lag, a user's pain/discomfort and/or the creation of persistent skin blemishes. For example, the pressure ring(s) 28 can be deployed (i.e., positioned such that pressure is applied to a user's skin layer in the vicinity of a target site) for a period of from 30 seconds to 3 hours and can then be retracted (i.e., positioned such that pressure is not being applied to the user's skin layer) for a period ranging from 30 seconds to 3 hours. Moreover, it has been determined that ISF glucose lag and a user's pain/discomfort are significantly reduced when the amount of time during which pressure is applied (i.e., the time period during which at least one pressure ring is deployed) is in the range of about 30 seconds to about 10 minutes and the amount of time during which pressure is released (i.e., the time period during which the at least one pressure ring is retracted) is in the range of about 5 minutes to 10 minutes. A particularly beneficial pressure ring cycle includes the application of pressure for one minute and the release of pressure for 10 minutes. Since different amounts of time are used for applying and releasing pressure, such a cycle is referred to as an asymmetric pressure ring cycle.

Pressure ring cycling routines can be devised such that the following concerns are balanced: (i) having the pressure ring(s) deployed for a time period that is sufficient to extract a desired volume of bodily fluid, (ii) inducing a physiological response that mitigates ISF glucose lag, and (iii) minimizing user discomfort and the creation of persistent blemishes. In addition, pressure ring cycling routines can also be devised to provide for semi-continuous analyte measurements that occur, for example, every 15 minutes.

Pressure ring(s) 28 can be formed of any suitable material known to those of skill in the art. For example, the pressure ring(s) 28 can be composed of a relatively rigid material, including, but not limited to, acrylonitrile butadiene styrene plastic material, injection moldable plastic material, polystyrene material, metal or combinations thereof. The pressure ring(s) 28 can also be composed of relatively resiliently deformable material, including, but not limited to, elastomeric materials, polymeric materials, polyurethane materials, latex materials, silicone materials or combinations thereof.

An interior opening defined by the pressure ring(s) 28 can be in any suitable shape, including but not limited to, circular, square, triangular, C-shape, U-shape, hexagonal, octagonal and crenellated shape.

When pressure ring(s) 28 is being employed to minimize ISF flow decay and/or control the flow of ISF through the sampling and analysis modules, penetration member 22 remains deployed in (i.e., residing in) the target site of the user's skin layer while the pressure ring(s) 28 is/are in use. However, when pressure ring(s) 28 are being employed to mitigate ISF glucose lag, the penetration member 22 can intermittently reside in the user's skin layer. Such intermittent residence of the penetration member 22 can occur either in or out of concert with the application of pressure by the pressure ring(s) 28.

Figure 3:
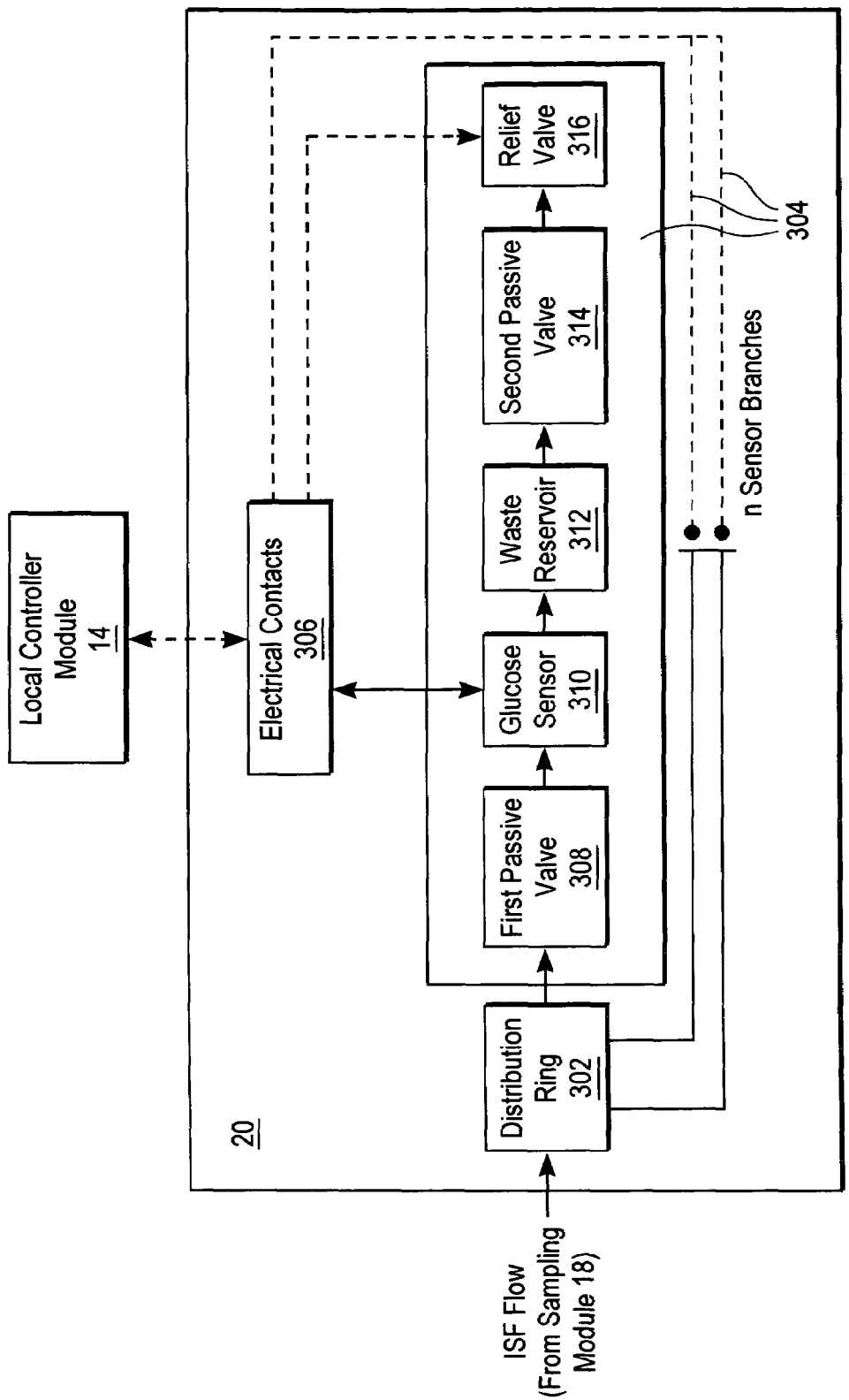
FIG. 3 is a simplified block diagram of an analysis module and local controller module according to an exemplary embodiment the present invention.

Referring to FIG. 3, analysis module 20 of system 10 includes a distribution ring 302, a plurality of micro-fluidic networks 304 and a plurality of electrical contacts 306. Each of micro-fluidic networks 302 includes a first passive valve 308, a glucose sensor 310, a waste reservoir 312, a second passive valve 314 and a relief valve 316. Micro-fluid networks 304 include channels with a cross-sectional dimension in the range of, for example, 30 to 500 micrometers. For monitoring (e.g., measuring) glucose in a flowing ISF sample, a plurality (n) of essentially identical micro-fluidic networks 304 (also referred to as sensor branches 304) can be included in analysis module 20. Distribution ring 302, first passive valve 308, waste reservoir 312, second passive valve 314 and a relief valve 316 are configured to control ISF flow through analysis module 20.

Any suitable glucose sensor known to those of skill in the art can be employed in analysis modules according to the present invention. Glucose sensor 310 can contain, for example, a redox reagent system including an enzyme and a redox active compound(s) or mediator(s). A variety of different mediators are known in the art, such as ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, and ruthenium complexes. Suitable enzymes for the assay of glucose in whole blood include, but are not limited to, glucose oxidase and dehydrogenase (both NAD and PQQ based). Other substances that may be present in the redox reagent system include buffering agents (e.g., citraconate, citrate, malic, maleic, and phosphate buffers); divalent cations (e.g., calcium chloride, and magnesium chloride); surfactants (e.g., Triton, Macol, Tetronic, Silwet, Zonyl, and Pluronic); and stabilizing agents (e.g., albumin, sucrose, trehalose, mannitol and lactose).

In the circumstance that glucose sensor 310 is an electrochemical based glucose sensor, glucose sensor 310 can produce an electrical current signal in response to the presence of glucose in an ISF sample. Local controller module 14 can then receive the electrical current signal (via electrical contacts 306) and convert it into ISF glucose concentration.

System 10 can be employed for the continuous and/or semi-continuous measurement (monitoring) of glucose in an ISF sample for a period of eight hours or more. However, conventional glucose sensors that can be economically mass-produced provide an accurate measurement signal for a lifetime of only about one hour. In order to overcome this problem of limited sensor lifetime, a plurality of micro-fluid networks 304, each containing an identical glucose sensor 310, are provided in analysis module 20. Each of these glucose sensors is employed in a consecutive manner to provide continuous and/or semi-continuous monitoring for a period of more than one hour.

The consecutive use of identical glucose sensors (each for a limited period of time, such as one hour) enables a continuous or semi-continuous measurement of glucose. The consecutive use of identical glucose sensors can be implemented by guiding an incoming flow of ISF from a sampling module towards a glucose sensor 310 for a period of time, followed by interrupting the ISF flow to that glucose sensor and switching the ISF flow to another glucose sensor. This consecutive use of glucose sensors can be repeated until each glucose sensor included in an analysis module has been used.

The switching of the ISF flow to consecutive glucose sensors can be accomplished, for example, by the following procedure. Upon initialization of analysis module 20, an ISF sample from sampling module 18 is distributed via distribution ring 302 to "n" sensor branches 304. However, the flow of ISF is halted at an inlet end of each sensor branch by the first passive valve 308 of each sensor branch. To start the measurement of glucose, a selected sensor branch is activated by opening the relief valve 316 of that sensor branch. The process of opening a selected relief valve can be electrically controlled by local controller module 14, which communicates with analysis module 20 via electrical contacts 306. Upon opening of a relief valve 316, gas (e.g., air) that is initially present in the sensor branch 304 (which is hermetically sealed) escapes at an outlet end of the sensor branch 304, and, as a result, ISF will flow into that sensor branch 304. As the relief valves 316 of the other sensor branches 304 remain closed, the ISF is allowed to flow only into the selected sensor branch 304.

The pressure of the ISF is sufficiently large to breach first passive valve 308 and will, therefore, flow towards glucose sensor 310. A measurement signal is subsequently created by glucose sensor 310 and communicated electronically via electrical contacts 306 to the local controller module 14 (as depicted by the dashed arrows in FIG. 3). ISF continues flowing and enters waste reservoir 312, the volume of which is predetermined such that it can contain an amount of ISF equivalent to that needed through the glucose sensor's lifetime. For example, at the average flow rate of about 50 nanoliters per minute and a glucose sensor lifetime of one hour, the volume of waste reservoir 312 would be approximately 3 microliters. A second passive valve 314 is located at the end of the waste reservoir 312. The second passive valve 314 is configured to stop the flow of ISF.

The procedure then continues by opening of a relief valve 316 of another sensor branch 304. Upon selectively opening this relief valve 316 (which can be accomplished via communication by the local controller module 14), ISF will flow into the corresponding sensor branch 304 after breaching the first passive valve 308 located in that sensor branch. Thereafter, the glucose sensor 310 of that sensor branch will provide a measurement signal to analysis module 20.

This procedure is repeated until all sensor branches 304 of analysis module 20 have been used. For a system to provide about eight hours of continuous glucose monitoring, about eight sensor branches 304 will be required in analysis module 20. It will be appreciated by those skilled in the art, however, that the analysis module 20 of disposable cartridge 12 is not limited to eight sensor branches and that, therefore, the system can be designed to measure ISF glucose levels for longer (or even shorter) than eight hours.

Figure 4:
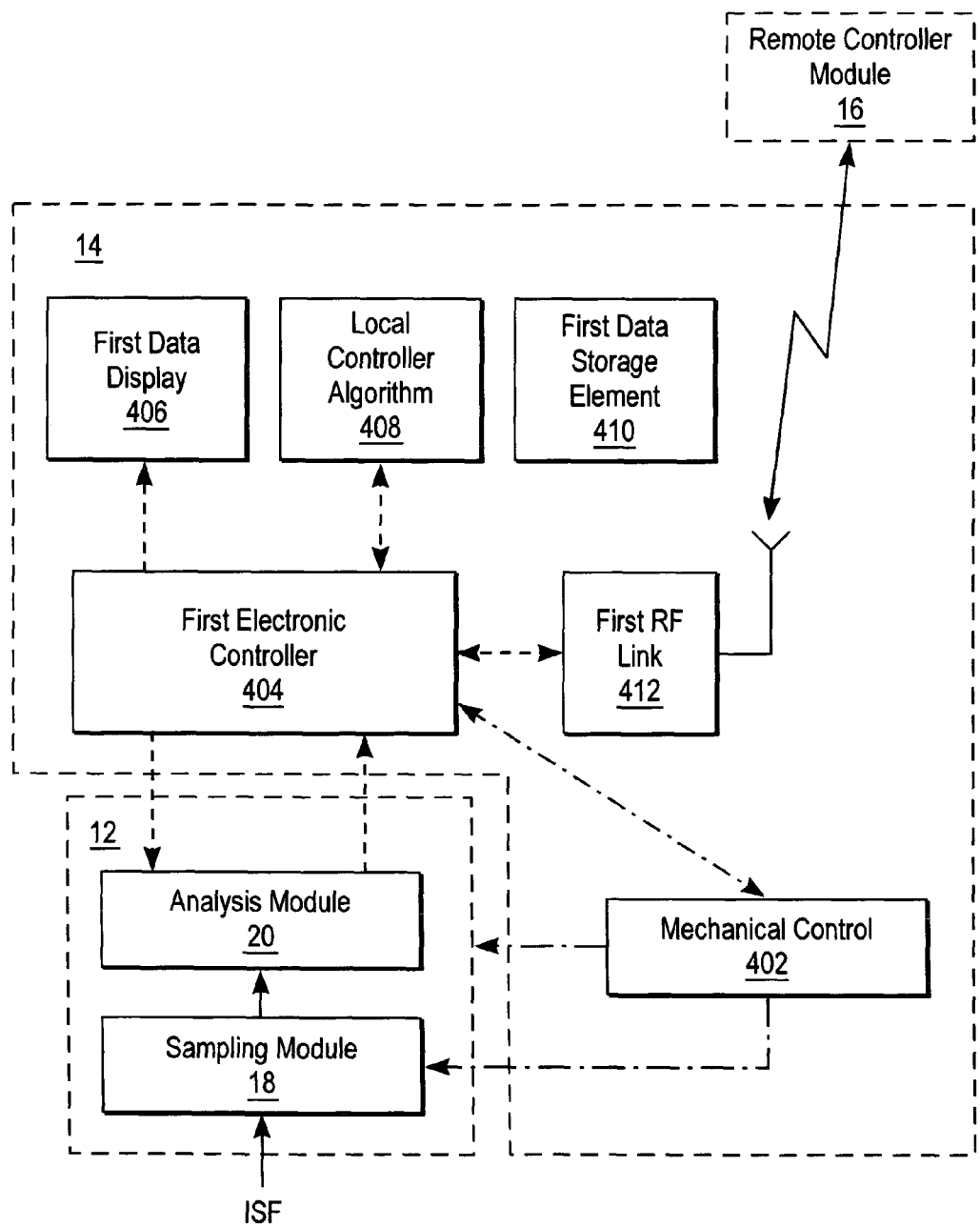
FIG. 4 is a simplified block diagram of an analysis module, local controller module and remote controller module according to an exemplary embodiment of the present invention.

Local controller module 14 is depicted in simplified block form in FIG. 4. Local controller module 14 includes a mechanical controller 402, a first electronic controller 404, a first data display 406, a local controller algorithm 408, a first data storage element 410 and a first RF link 412.

Local controller module 14 is configured such that it can be electrically and mechanically coupled to disposable cartridge 12. The mechanical coupling provides for disposable cartridge 12 to be removably attached to (e.g., inserted into) local controller module 14. Local controller module 14 and disposable cartridge 12 are configured such that they can be attached to the skin of a user by, for example, a strap, in a manner which secures the combination of the disposable cartridge 12 and local controller module 14 onto the user's skin.

During use of system 10, first electronic controller 404 controls the measurement cycle of the analysis module 20, as described above. Communication between local controller module 14 and disposable cartridge 12 takes place via electrical contacts 306 of analysis module 20 (see FIG. 3).

Electrical contacts 306 can be contacted by contact pins 708 (see FIG. 7) of the local controller module 14. Electrical signals are sent by the local controller module 14 to analysis module 20 to, for example, selectively open relief valves 316. Electrical signals representing the glucose concentration of an ISF sample are then sent by the analysis module to the local controller module. First electronic controller 404 interprets these signals by using the local controller algorithm 408 and displays measurement data on a first data display 406 (which is readable by the user). In addition, measurement data (e.g., ISF glucose concentration data) can be stored in first data storage element 410.

Prior to use, an unused disposable cartridge 12 is inserted into local controller module 14. This insertion provides for electrical communication between disposable cartridge 12 and local controller module 14. A mechanical controller 402 in the local controller module 14 securely holds the disposable cartridge 12 in place during use of system 10.

After attachment of a local controller module and disposable cartridge combination to the skin of the user, and upon receiving an activation signal from the user, a measurement cycle is initiated by first electronic controller 404. Upon such initiation, penetration member 22 is launched into the user's skin layer to start ISF sampling. The launching can be initiated either by first electronic controller 404 or by mechanical interaction by the user.

First RF link 412 of local controller module 14 is configured to provide bi-directional communication between the local controller module and a remote controller module 16, as depicted by the jagged arrows of FIGS. 1 and 4. The local controller module incorporates a visual indicator (e.g., a multicolor LED) indicating the current status of the system.

Local controller module 14 is configured to receive and store measurement data from, and to interactively communicate with, disposable cartridge 12. For example, local controller module 14 can be configured to convert a measurement signal from analysis module 20 into an ISF or blood glucose concentration value.

Figure 5:
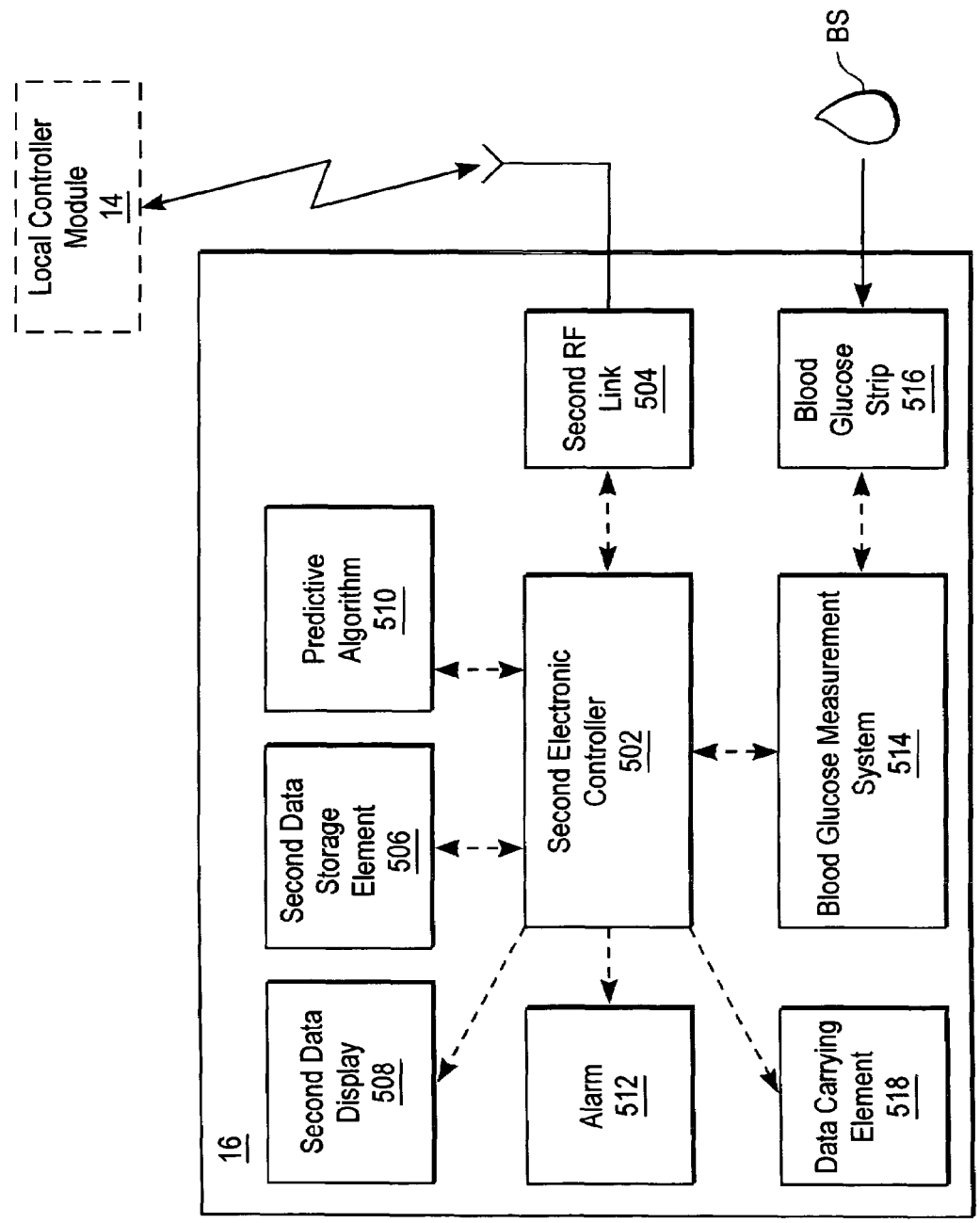
FIG. 5 is a simplified block diagram of a remote controller module according to an exemplary embodiment of the present invention.

FIG. 5 shows a simplified block diagram depicting remote controller module 16 of system 10. Remote controller module 16 includes a second electronic controller 502, a second RF link 504, a second data storage element 506, a second data display 508, a predictive algorithm 510, an alarm 512, a blood glucose measurement system (adapted to measure blood glucose utilizing blood glucose strip 516) and a data carrying element 518.

Second electronic controller 502 is adapted to control various components of remote controller module 16. Second RF link 504 is configured for bi-directional communication with the local controller module 14 (e.g., second RF link 504 can receive ISF glucose concentration related data from local controller module 14). Data received via second RF link 504 can be validated and verified by second electronic controller 502. Furthermore, the data so received can also be processed and analyzed by second electronic controller 502 and stored in second data storage element 506 for future use (e.g., future data retrieval by a user or for use in predictive algorithm 510). Second data display 508 of remote controller module 16 can be, for example, a graphic LCD display configured to present measurement data in a convenient format to a user and to present an easy to use interface for further data management.

The local controller module 14 is adapted to communicate via second RF link 504 to a remote controller module 16. Functions of remote controller module 16 include the displaying, storing and processing of glucose measurement data in a presentable and convenient format for the user. Remote controller module 16 can also provide an (audible, visual and/or vibratory) alarm via alarm 512 for warning the user of deleterious glucose concentrations. A further function of remote controller module 16 is to measure a user's blood glucose concentration using blood glucose measurement system 514 and a single use blood glucose measurement strip 516. Blood glucose values measured by blood glucose measurement system 514 can be used to verify blood glucose values calculated by predictive algorithm 510. Remote controller module 16 can also be configured to provide for user specific data (e.g., event tags, state of mind and medical data) to be entered and parsed.

Remote controller module 16 is configured as a portable unit and to communicate with local controller module 14 (e.g., to receiving glucose measurement data from local controller module 14). Remote controller module 16, therefore, provides a user with a simple and convenient platform for managing glucose monitoring-related data (e.g., storing, displaying and processing of glucose monitoring-related data) and can be used to fine tune therapy (i.e., insulin administration). Functions of the remote controller module 16 can include the gathering, storing and processing of ISF glucose data and the display of the blood glucose value calculated from ISF glucose data. By incorporating such functions in remote controller module 16, rather than local controller module 14, the size and complexity of local controller module 14 are reduced. However, if desired, the remote controller module functions described above can be alternatively performed by the local controller module.

In order to facilitate a measurement of the blood glucose level in a blood sample (BS), blood glucose measurement system 514 is provided as an integral part of the remote controller module 16. The blood glucose measurement system 514 makes a measurement with a blood glucose strip 516, on which a blood sample (e.g., a drop of blood) has been placed. The resulting blood glucose measurement can be compared to glucose values calculated by predictive algorithm 510.

Remote controller module 16 can optionally incorporate a communication port, such as a serial communication port (not shown in FIG. 5). Suitable communication ports are known in the art, for example, an RS232 (IEEE standard) and a Universal Serial Bus. Such communication ports can be readily adopted for exporting stored data to an external data management system. Remote controller module 16 also incorporates a programmable memory portion (not shown in FIG. 5), such as a reprogrammable flash memory portion, that can be programmed via a communication port. A purpose of such a memory portion is to facilitate updates of an operating system and/or other software element of the remote controller module via communication through the communication port.

The remote controller module 16 can further include a communication slot (not shown) for receiving a data carrying element 518 and communicating therewith. Data carrying element 518 can be any suitable data carrying element known in the art, such as a 'SIM' data carrying element, also known as "smart-chip."

Data carrying element 518 can be provided with a disposable cartridge 12 and can contain disposable cartridge production lot specific data, such as calibration data and lot identification number. The remote controller module 16 can read the data contained on data carrying element 518 and such data can be employed in the interpretation of the ISF glucose data received from the local controller module 14. Alternatively, the data on data carrying element 518 can be communicated to the local controller module 14 via second RF link 504 and can be used in data analysis performed by the local controller module 14.

The second electronic controller 502 of remote controller module 16 is configured to interpret data, as well as to perform various algorithms. One particular algorithm is predictive algorithm 510 for predicting near future (within 0.5-1 hour) glucose levels. As there is a time difference ("lag time") between changes of glucose concentration in the blood of the user and the corresponding change of glucose concentration in the ISF of the user, predictive algorithm 510 uses a series of mathematical operations performed on the stored measurement data to take into account user specific parameters reflecting individual lag time relationships. The outcome of the predictive algorithm 510 is an estimation of the blood glucose level based on the ISF glucose level. If the predictive algorithm 510 predicts low glucose levels, a signal can be raised and alarm 512 activated to warn the user of a predicted physiological event such as hypoglycemia or risk of coma. As will be appreciated by those skilled in the art, the alarm 512 may be comprised of any suitable signal including an audible, visual or vibratory signal, warning either the user directly or the user's health care provider. An audible signal is preferred, as it will wake up a sleeping user encountering a hypoglycemic event.

The difference between an ISF glucose value (concentration) at any given moment in time and a blood glucose value (concentration) at the same moment in time is referred to as the ISF glucose lag. ISF glucose lag can be conceivably attributed to both physiological and mechanical sources. The physiological source of lag in ISF glucose is related to the time it takes for glucose to diffuse between the blood and interstices of a user's skin layer. The mechanical source of lag is related to the method and device used to obtain an ISF sample.

Embodiments of devices, systems and methods according to the present invention mitigate (reduce or minimize) ISF glucose lag due to physiological sources by applying and releasing pressure to a user's skin layer in an oscillating manner that enhances blood flow to a target area of the user's skin layer. ISF extraction devices that include pressure ring(s) according to the present invention (as described in detail below) apply and release pressure in this manner. Another approach to account for lag in ISF glucose is to employ an algorithm (e.g., predictive algorithm 510) that predicts blood glucose concentration based on measured ISF glucose concentrations.

Predictive algorithm 510 can, for example, take the general form:

$$\text{Predicted blood glucose} = f(ISF_i^k, \text{rate}_j, \text{ma}_n\text{rate}_m^p, \text{interaction terms})$$

where:

i is an integer of value between 0 and 3;

j, n, and m are integers of value between 1 and 3;

k and p are integers of value 1 or 2;

$ISF_i$ is a measured ISF glucose value with the subscript (i) indicating which ISF value is being referred to, i.e., 0=current value, 1=one value back, 2=two values back, etc.;

$\text{rate}_j$ is the rate of change between adjacent ISF values with the subscript (i) referring to which adjacent ISF values are used to calculate the rate, i.e., 1=rate between current ISF value and the previous ISF value, 2=rate between the ISF values one previous and two previous relative to the current ISF value, etc.; and $\text{ma}_n\text{rate}_m$ is the moving average rate between adjacent averages of groupings of ISF values, with the subscripts (n) and (m) referring to (n) the number of ISF values included in the moving average and (m) the time position of the moving adjacent average values relative to the current values as follows.

The general form of the predictive algorithm is a linear combination of all allowed terms and possible cross terms, with coefficients for the terms and cross terms determined through regression analysis of measured ISF values and blood glucose values at the time of the ISF sample acquisition. Further details regarding predictive algorithms suitable for use in systems according to the present invention are included in U.S. patent application Ser. No. 10/652,464, which is hereby incorporated by reference.

As will also be appreciated by those skilled in the art, the outcome of the predictive algorithm can be used to control medical devices such as insulin delivery pumps. A typical example of a parameter that can be determined based on the algorithm outcome is the volume of a bolus of insulin to be administered to a user at a particular point in time.

Figure 6:
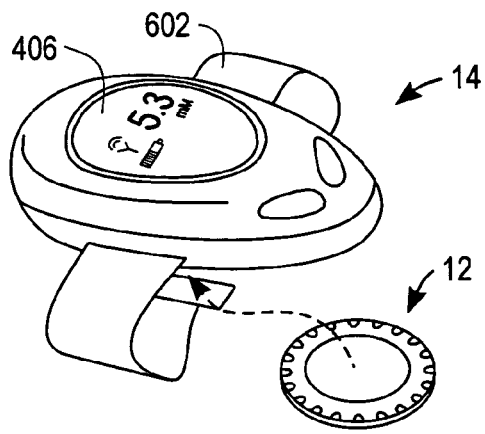
FIG. 6 is a top perspective view of a disposable cartridge and local controller module according to an exemplary embodiment of the present invention.
Figure 7:
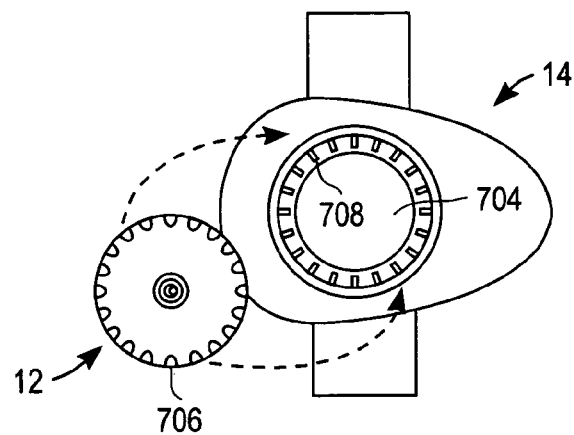
FIG. 7 is a bottom perspective view of the disposable cartridge and local controller module of FIG. 6.
Figure 8:
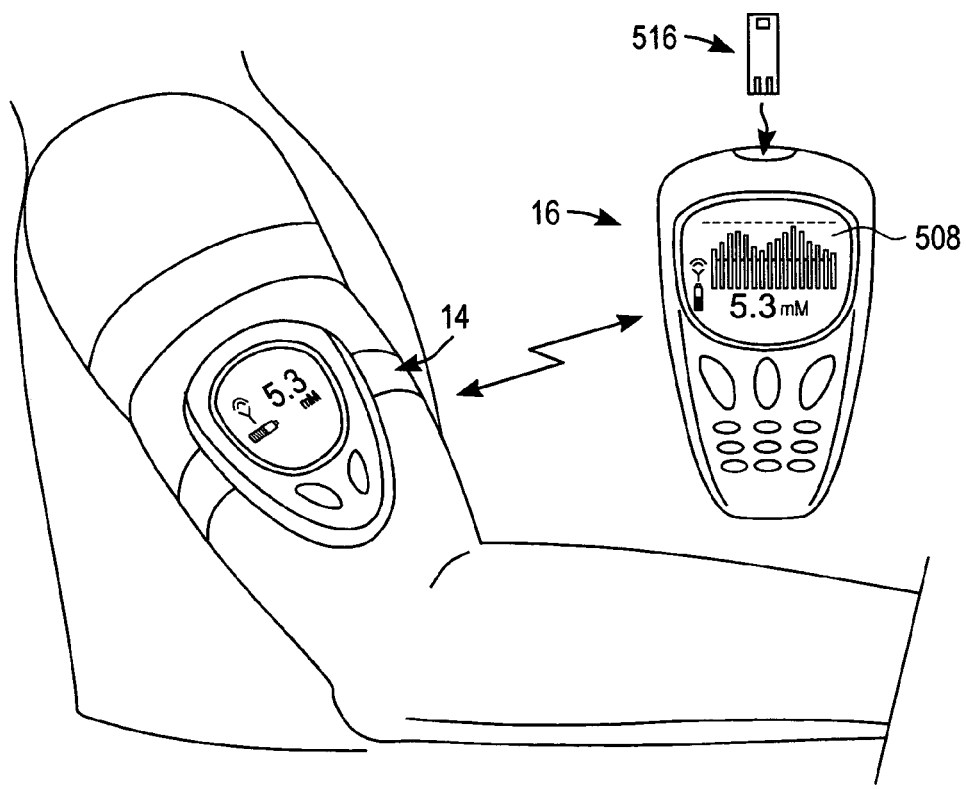
FIG. 8 is a perspective view of a system according to another exemplary embodiment of the present invention with the disposable cartridge and local controller module attached to an arm of a user.

The combination of local controller module 14 and disposable cartridge 12 can be configured to be worn on the skin of a user in order to simplify sampling and monitoring of ISF extracted from the user's skin layer (see FIGS. 6-8).

During use of the system embodiment of FIGS. 1-10, disposable cartridge 12 is located within and controlled by local controller module 14. In addition, the combination of disposable cartridge 12 and local controller module 14 is configured to be worn by a user, preferably on the upper part of the user's arm or forearm. The local controller module 14 is in electrical communication with the disposable cartridge 12 for purposes of measurement control and for receiving measurement data from the analysis module.

Referring to FIG. 6, local controller module 14 includes a first data display 406 and a pair of straps 602 for attachment of the local controller module 14 to the arm of a user. FIG. 6 also depicts disposable cartridge 12 prior to insertion into local controller module 14.

FIG. 7 shows a bottom view of the local controller module 14 prior to the insertion of the disposable cartridge 12 into an insertion cavity 704 provided in local controller module 14. The disposable cartridge 12 and local controller module 14 are configured such that disposable cartridge 12 is secured within the insertion cavity 704 by mechanical force. In addition, the local controller module 14 and the disposable cartridge 12 are in electrical communication via a set of molded contact pads 706 that are provided on disposable cartridge 12. These molded contact pads 706 are in registration with a set of contact pins 708 provided within the insertion cavity 704 of the local controller module 14 when the disposable cartridge is inserted into insertion cavity 704.

FIG. 8 shows the local controller module 14 after insertion of the disposable cartridge 12 into local controller module 14 and attachment of the combination of the disposable cartridge and local controller module onto the arm of a user. FIG. 8 also depicts a remote controller module 16 located within RF communication range of the local controller module 14.

Figure 9:
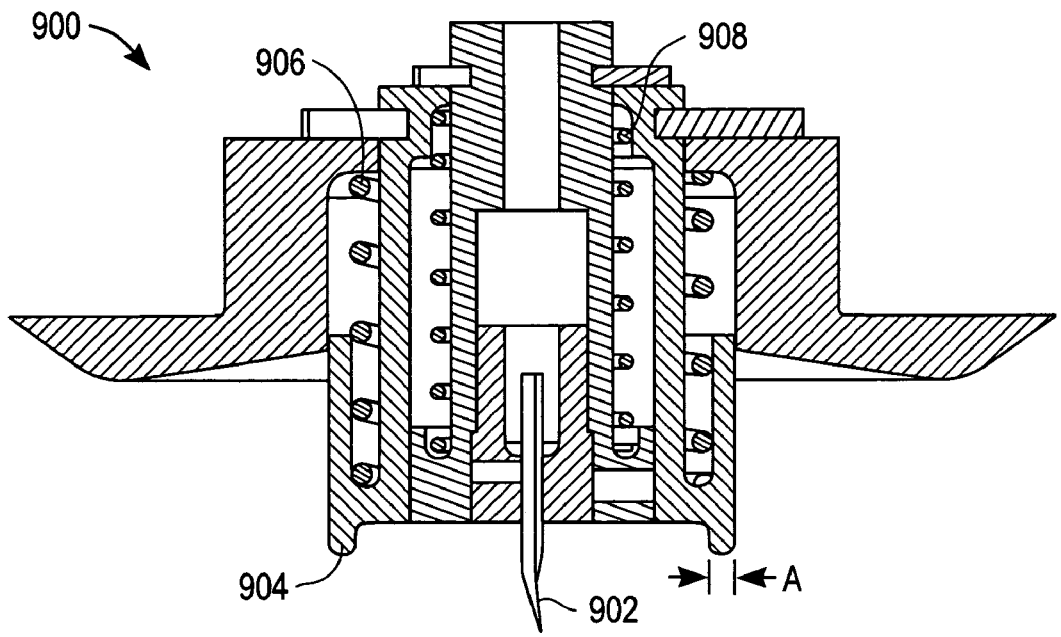
FIG. 9 is a simplified cross-sectional side view of an extraction device according to an exemplary embodiment of the present invention.

FIG. 9 is a cross-sectional side view of an interstitial fluid (ISF) extraction device 900 according to an exemplary embodiment of the present invention. ISF extraction device 900 includes a penetration member 902, a pressure ring 904, a first biasing member 906 (i.e., a first spring) and a second biasing member 908 (namely, a second spring).

Penetration member 902 is configured for penetration of a user's skin layer at a target site and for the subsequent extraction of ISF therefrom. Penetration member 902 is also configured to remain in (reside in) the user's skin layer during the extraction of ISF therefrom. Penetration member 902 can, for example, remain in the user's skin layer for more than one hour, thus allowing a continuous or semi-continuous extraction of ISF. Once apprised of the present disclosure, one skilled in the art will recognize that the penetration member can reside in the user's skin layer for an extended period of time of 8 hours or more.

Pressure ring 904 is configured to oscillate between a deployed state and a retracted state. When pressure ring 904 is in the deployed state, it applies pressure to the user's skin layer surrounding the target site, while the penetration member is residing in the user's skin layer in order to (i) facilitate the extraction of ISF from the user's skin layer and (ii) control the flow of ISF through ISF extraction device 900 to, for example, an analysis module as described above. When pressure ring 904 is in a retracted state, it applies either a minimal pressure or no pressure to the user's skin layer surrounding the target site. Since pressure ring 904 can be oscillated between a deployed state and a retracted state, the time that any given portion of a user's skin layer is under pressure can be controlled, thereby providing for the user's skin layer to recover and reducing pain and blemishes.

Pressure ring 904 typically has, for example, an outside diameter in the range of 0.08 inches to 0.56 inches and a wall thickness (depicted as dimension "A" in FIG. 9) in the range of 0.02 inches to 0.04 inches.

First biasing element 906 is configured to urge pressure ring 904 against the user's skin layer (i.e., to place pressure ring 904 into a deployed state) and to retract pressure ring 904. Second biasing element 908 is configured to launch the penetration member 902 such that the penetration member penetrates the target site.

The pressure (force) applied against a user's skin layer by the pressure ring(s) can be, for example, in the range of from about 1 to 150 pounds per square inch (PSI, calculated as force per cross-sectional pressure ring area). In this regard, a pressure of approximately 50 PSI has been determined to be beneficial with respect to providing adequate ISF flow while minimizing user pain/discomfort.

In the embodiment of FIG. 9, penetration member 902 is partially housed in a recess of the oscillating pressure ring 904, the depth of the recess determining the maximum penetration depth of the penetration member 902. Although not explicitly shown in FIG. 9, the penetration member 902 and the oscillating pressure ring 904 can be moved relative to one another and applied to a user's skin layer independent of each other.

During use of ISF extraction device 900, the oscillating pressure ring 904 can be deployed for stabilizing the user's skin layer and to isolate and pressurize a region of the target area and thus to provide a net positive pressure to promote flow of ISF through penetration member 902.

If desired, ISF extraction device 900 can contain a penetration depth control element (not shown) for limiting and controlling the depth of needle penetration during lancing. Examples of suitable penetration depth control elements and their use are described in U.S. patent application Ser. No. 10/690,083, which is hereby fully incorporated herein by reference.

During use of ISF extraction device 900, a system that includes ISF extraction device 900 is placed against a user's skin layer with the pressure ring 904 facing the skin (see, for example, FIG. 8). The pressure ring 904 is urged against the skin to create a bulge. The bulge is then penetrated (e.g., lanced) by the penetration member 902. An ISF sample is subsequently extracted from the bulge while the penetration member 902 remains totally or partially within the skin.

The flow rate of the ISF sample being extracted is initially relatively high but typically declines over time. After a period in the range of 3 seconds to 3 hours, pressure ring 904 can be retracted to allow the skin to recover for a period of about 3 seconds to 3 hours. Pressure ring 904 can then be re-deployed for a period in the range of about 3 seconds to about 3 hours and retracted for about 3 seconds to 3 hours. This process of deploying and retracting pressure ring 904 proceeds until ISF extraction is discontinued. The deployment and retraction cycles are preferably asymmetric in that different periods of time are used for each cycle.

Figure 10:
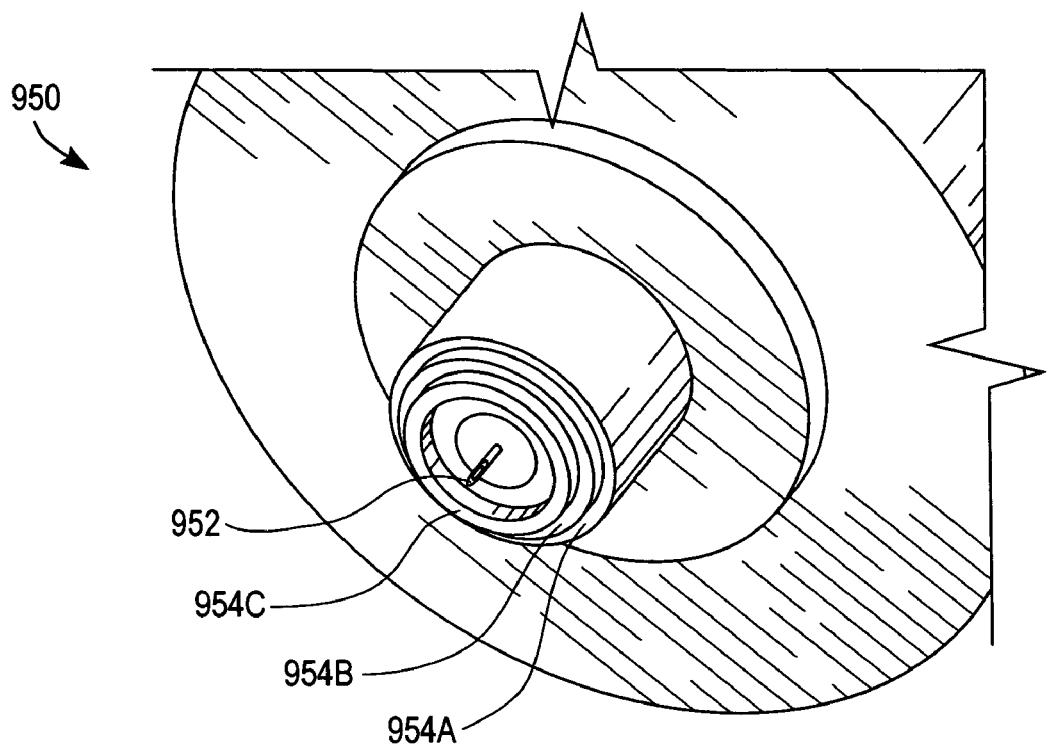
FIG. 10 is a perspective view of a portion of an extraction device according to yet another exemplary embodiment of the present invention.
Figure 11:
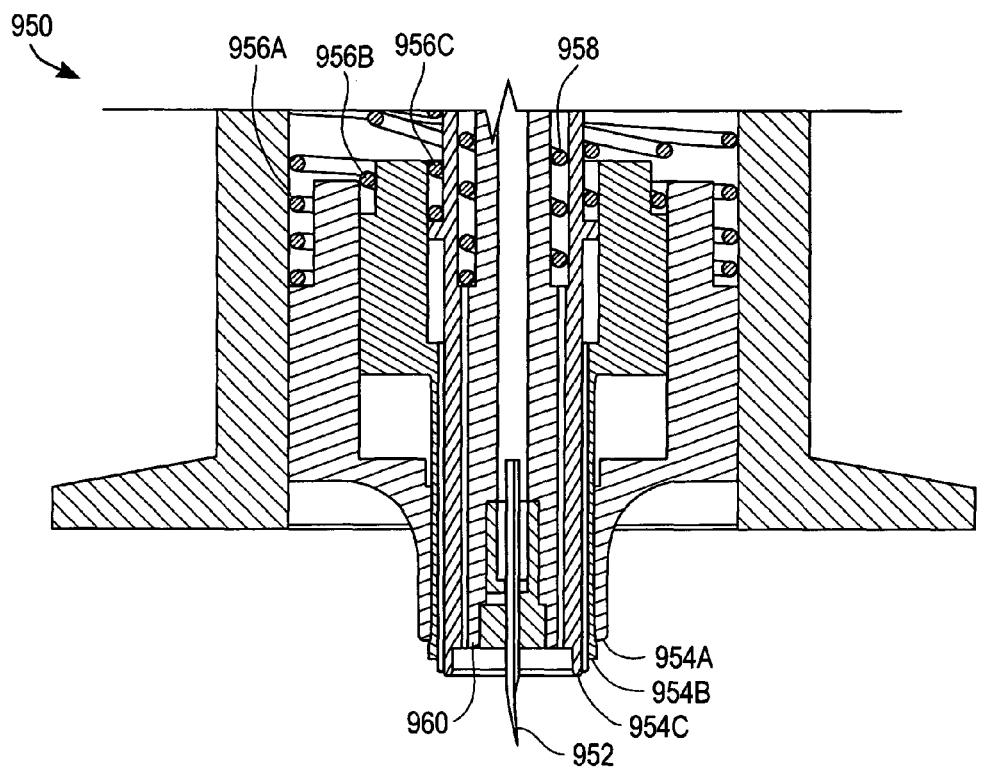
FIG. 11 is a simplified cross-sectional side view of the extraction device of FIG. 10.

FIGS. 10 and 11 are cross sectional and perspective views, respectively, of an ISF extraction device 950 according to another exemplary embodiment of the present invention. ISF extraction device 950 includes a penetration member 952 and a plurality of concentrically arranged pressure rings 954A, 954B and 954C. ISF extraction device 950 also includes a plurality of first biasing elements 956A, 956B and 956C for urging the pressure rings 954A, 954B and 956C, respectively, toward and against a user's skin layer, a second biasing element 958 for launching the penetration member 952, and a penetration depth control element 960.

During use, ISF extraction device 950 is positioned such that pressure rings 954A, 954B and 954C are facing a user's skin layer. This can be accomplished, for example, by employing ISF extraction device 950 in a sampling module of a system for extracting bodily fluid as described above and placing the system against the user's skin layer.

Pressure ring 954A is then urged against the user's skin layer by biasing element 956A, thereby creating a bulge in the user's skin layer that will subsequently be lanced (i.e., penetrated) by penetration member 952. While pressure ring 954A is in use (i.e., deployed), pressure ring 954B and pressure ring 954C can be maintained in a retracted position by biasing elements 956B and 956C, respectively.

ISF can be extracted from the bulge formed in user's skin layer while the penetration member 952 resides totally or partially within the user's skin layer. After about 3 seconds to 3 hours, the pressure ring 954A can be retracted to allow the user's skin layer to recover for a time period in the range of about 3 seconds to 3 hours. After retracting the pressure ring 954A, pressure ring 954B can be deployed to apply pressure on the user's skin layer. While pressure ring 954B is in use (i.e., deployed), pressure ring 954A and pressure ring 954C can be maintained in a retracted position by biasing elements 956A and 956C, respectively. After a time period of about 3 seconds to 3 hours, pressure ring 954B can be retracted for a time period in the range of 3 seconds to 3 hours, followed by the deployment of pressure ring 954C. Pressure ring 954C maintains pressure on the user's skin layer for a time period in the range of 3 seconds to 3 hours and is then retracted for a time period in the range of 3 seconds to 3 hours. While pressure ring 954C is in use (i.e., deployed), pressure ring 954A and pressure ring 954B can be maintained in a retracted position by biasing elements 956A and 956B, respectively. This process of cycling between deployment and retraction of pressure rings 954A, 954B and 954C can proceeds until fluid extraction has ended. As with the embodiment shown in FIG. 9, the deployment and retraction cycles in the multiple pressure ring embodiment of FIGS. 10 and 11 are preferably asymmetric in that different periods of time are used for each cycle.

Those skilled in the art will also recognize that a plurality of pressure rings in ISF extraction devices according to the present invention can be deployed in any order and that one is not limited to the deployment and retraction sequence described above. For example, a sequence can be used in which pressure ring 954B or 954C is applied before pressure ring 954A. Further, more than one pressure ring can be deployed simultaneously. For example, the embodiment shown in FIGS. 10 and 11 can deploy all three pressure rings simultaneously such that the pressure rings function as a single pressure ring.

For the embodiment shown in FIGS. 10 and 11, the pressure applied against the user's skin can, for example, range from about 0.1 to 150 pounds per square inch (PSI) for each of the plurality of pressure rings.

The pressure rings 954A, 954B and 954C can have, for example, outer diameters of in the range of 0.08 to 0.560 inches, 0.1 to 0.9 inches and 0.16 to 0.96 inches, respectively. The wall thickness of each pressure ring can be, for example, in the range of 0.02 to 0.04 inches.

Figure 14:
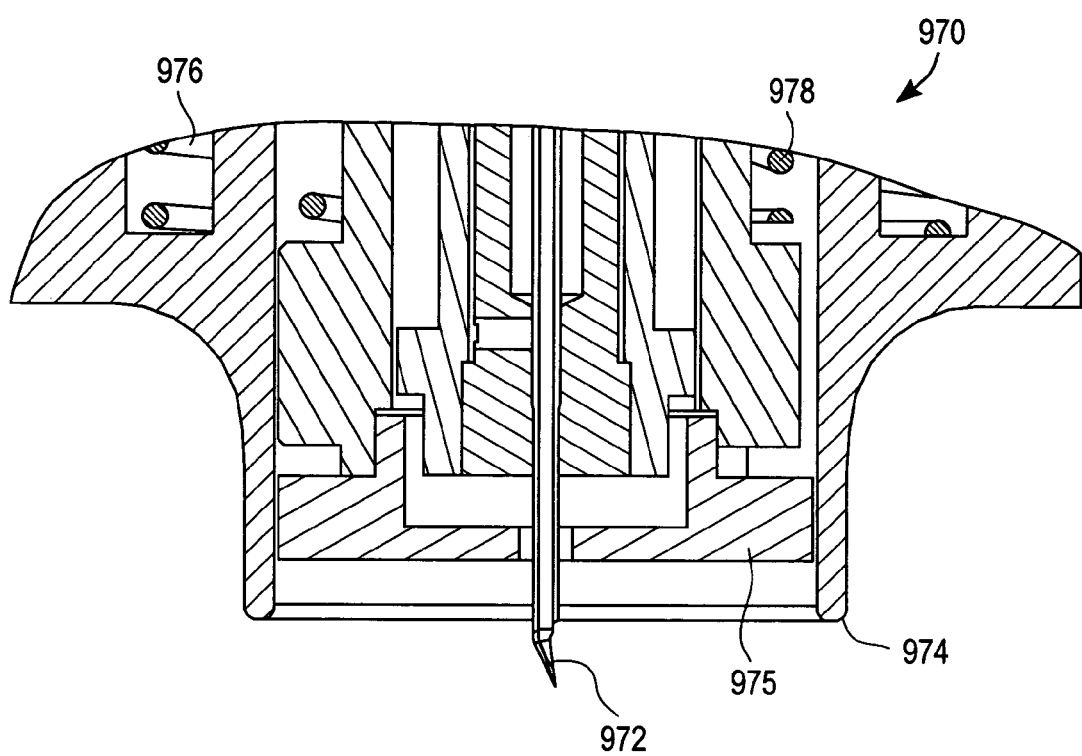
FIG. 14 is a simplified cross-sectional side view of a portion of an extraction device according a further embodiment of the present invention.

An inner-most pressure ring of extraction devices according to an alternative embodiment of the present invention can, if desired, be a flat ring (see FIG. 14) for the purpose of keeping the needle in the user's skin layer while applying negligible pressure to keep blood flowing to the area. FIG. 14 shows a cross-sectional side view of a portion of an interstitial fluid (ISF) extraction device 970 according to an alternative exemplary embodiment of the present invention. ISF extraction device 970 includes a penetration member 972, a pressure ring 974, a flat pressure ring 975, a first biasing member 976 (i.e., a first spring) for biasing the pressure ring 974 and a second biasing member 978 (namely, a second spring) for biasing the flat pressure ring.

In this alternate embodiment, the flat pressure ring surrounds the needle (i.e., the penetration member 972) and contains a hole of sufficient size to just allow the needle to pass through. The flat pressure ring preferably has a diameter of 0.02 to 0.56 inches.

Inclusion of at least one pressure ring in extraction devices according to the present invention provides a number of benefits. First, oscillating the pressure ring(s) between a deployed and retracted state serves to mitigate (i.e., reduce) ISF glucose lag. Upon retraction of the pressure ring(s), pressure on the user's skin layer is released, and the user's body reacts by increasing blood perfusion to the target site. This phenomenon is known as reactive hyperemia and is hypothesized to be a mechanism by which ISF is beneficially replenished in the target site by oscillation of the pressure ring(s). Such a replenishment of ISF helps mitigating the lag between the ISF glucose and whole blood glucose values.

Another benefit of ISF extraction devices according to the present invention is that oscillation of the pressure ring(s) allows the skin under the pressure ring(s) to recover, thus reducing a user's pain, discomfort and the creation of persistent blemishes.

Moreover, extraction devices with a plurality of pressure rings (e.g., the embodiment of FIGS. 10 and 11) can be used with at least one pressure ring permanently deployed to facilitate ISF collection while the other pressure rings are oscillated between deployed and retracted states so that different areas of the user's skin layer are under pressure at any given time. Such combination of permanently deployed pressure ring(s) and oscillated pressure ring(s) further aids in reducing a user's pain/discomfort.

Still another benefit of ISF extraction devices according to the present embodiment is that the pressure ring(s) can be used to control the conditions under which a glucose measurement of an extracted ISF sample is conducted. For example, an electrochemical glucose sensor is more accurate and precise if the ISF sample flow rate past the glucose sensor is constant or static. The pressure ring(s) of ISF extraction devices according to the present invention can provide a controlled flow of the extracted ISF sample. For example, retraction of the pressure ring(s) can stop ISF sample flow for a time period of 0.1 seconds to 60 minutes to allow a glucose concentration measurement to be conducted. Once the glucose concentration measurement is complete, one or more of the pressure rings can be redeployed to continue ISF extraction. In this manner, a semi-continuous ISF sample extraction can be accomplished.

Once apprised of the present disclosure, one skilled in the art will recognize that ISF extraction devices according to the present invention can be employed in a variety of systems including, but not limited to, systems for the extraction of a bodily fluid sample and monitoring of an analyte therein, as described above. For example, the ISF extraction devices can be employed in a sample module of such systems.

Figure 13:
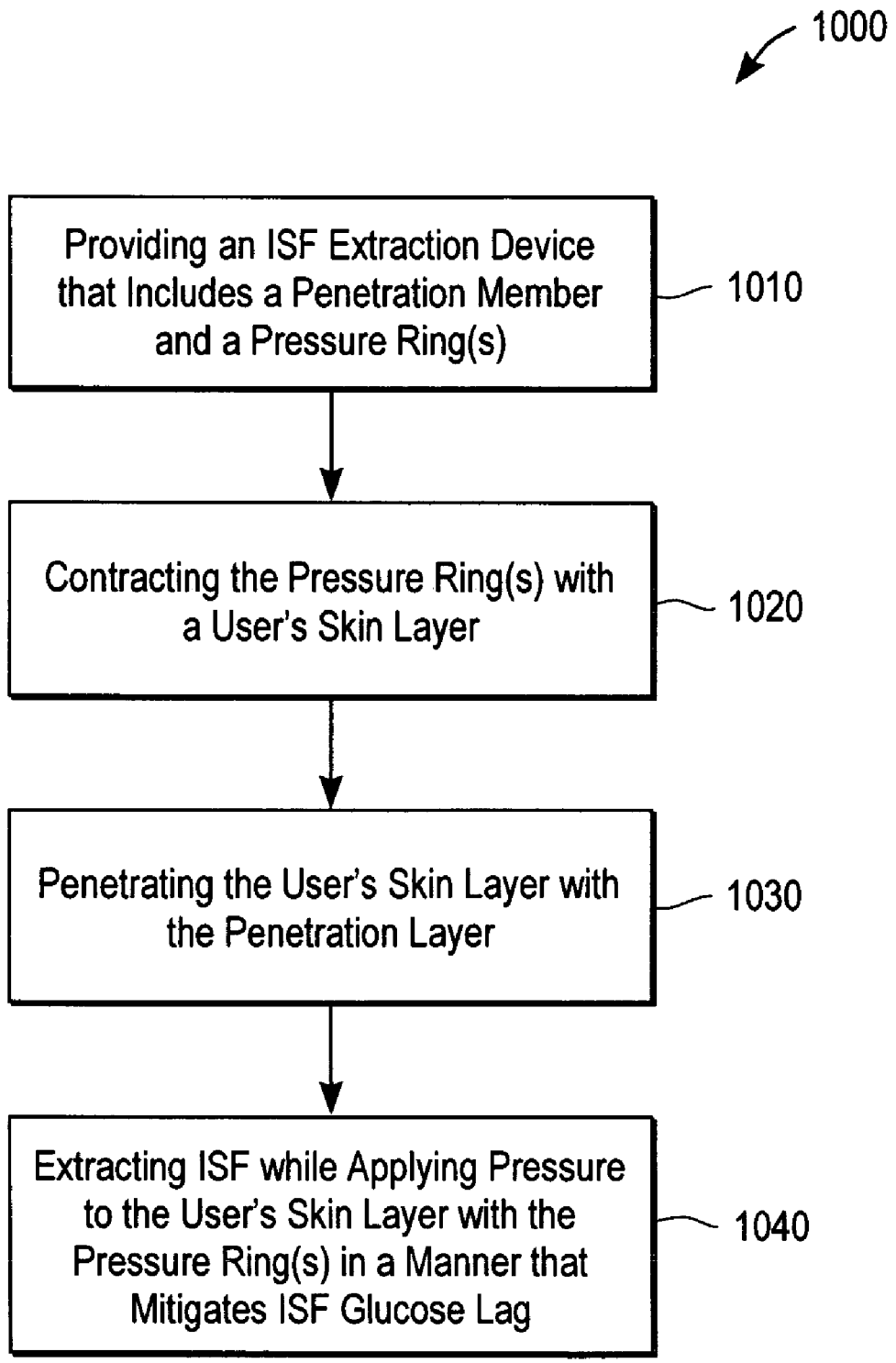
FIG. 13 is a flow diagram illustrating a sequence of steps in a process according to one exemplary embodiment of the present invention.

Referring to FIG. 13, a method 1000 for continuous collection of an ISF sample from a user's skin layer according to an exemplary embodiment of the present invention includes providing an ISF fluid extraction device, as set forth in step 1010. The ISF fluid extraction device that is provided includes a penetration member and at least one pressure ring (e.g., a single pressure ring or three concentric pressure rings). The penetration member and pressure ring(s) can be penetration members and pressure rings, as described above with respect to ISF extraction devices and systems according to the present invention.

Next, as set forth in step 1020, the pressure ring(s) is contacted with a user's skin layer in the vicinity of a target site (e.g., finger tip dermal tissue target site; a limb target site, an abdomen target site or other target site from which an ISF sample is to be extracted). The pressure ring can be contacted to the user's skin layer using any suitable techniques including, for example, those described above with respect to embodiments of systems and devices according to the present invention.

The target site of the user's skin layer is then penetrated by penetration member, as set forth in step 1030. Next, ISF is extracted from the user's skin layer by the penetration member while pressure is applied to the user's skin layer in an oscillating manner that mitigates an ISF lag of the extracted ISF, as set forth in step 1040. The various oscillating manners, by which pressure is applied, in methods according to the present invention have been described above with respect to FIGS. 1-12.

The following examples serve to illustrate beneficial aspects of various embodiments of devices, systems and methods according to the present invention.

EXAMPLE 1

Impact of an Oscillating Pressure Ring on Blood Perfusion in an Area within the Oscillating Pressure Ring Laser Doppler image perfusion data were collected at semi-regular intervals from a 0.25 square centimeter area approximately centered in the inside of a pressure ring attached to a subject's forearm. The pressure ring had an outside diameter of 0.53 inches and a wall thickness of 0.03 inches. Baseline data were collected prior to deploying the pressure ring against the subject's skin layer. The pressure ring was deployed against the skin layer for 10 minutes with a spring force of 0.5 lbs, retracted from the skin layer for 30 minutes, and then this cycle of deployment and retraction was repeated. The pressure ring was subsequently deployed against the skin layer for 5 hours, raised for 1 hour, and finally deployed against the skin for 10 minutes. The average perfusions in the 0.25 cm sq. measurement area are shown in the graph of FIG. 12.

Figure 12:
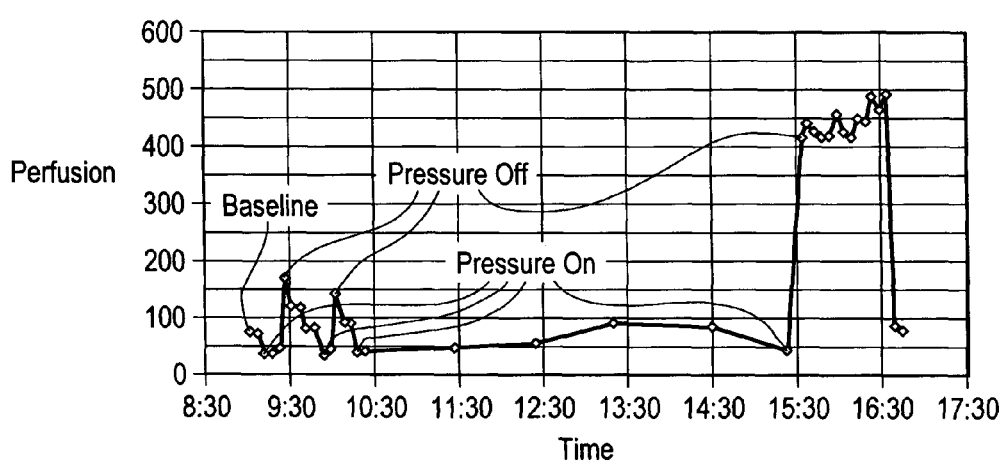
FIG. 12 is a graph showing perfusion as a function of time for a test conducted using the extraction device of FIG. 9.

As can be seen in the graph in FIG. 12, deployment of the pressure ring reduced blood perfusion in the area enclosed by the pressure ring (i.e., blood perfusion was reduced with the application of pressure), in comparison to the baseline blood perfusion. However, removing the pressure ring (i.e., releasing the pressure) not only reversed this effect, but actually increased perfusion beyond the baseline.

EXAMPLE 2

Impact of an Oscillating Pressure Ring on ISF Glucose Lag

A study was performed to determine the impact of blood flow on ISF glucose values during use of an oscillating pressure ring according to exemplary embodiments of the present invention. Twenty diabetic subjects underwent a procedure, in which baseline blood perfusion measurements were made on volar and dorsal portions of the subject's forearms. The subjects then participated in a test, in which finger blood samples, control ISF samples and treated ISF samples were collected at 15 minute intervals over a period of 3 to 6 hours. Control ISF samples were obtained from the subject's forearms without any skin layer manipulation and treated ISF samples were obtained by manipulating the subject's skin layer with an oscillating pressure ring. During the 3 to 6 hour testing period, blood glucose was influenced by ingestion of a microwave meal and diabetes medications including insulin and oral hypoglycemics such that most subjects experienced a rise and fall in blood glucose.

The treated ISF samples were created by applying approximately 150 pounds per square inch of pressure with a pressure ring with no sampling for 30 seconds, followed by a 5 minute waiting period to allow blood to perfuse into the sampling target site. Blood perfusion measurements were made with a Moor Laser Doppler Imager (Devon, UK) immediately prior to obtaining both control and treated ISF samples. Laser Doppler imaging was performed over a 2 square centimeter area centered on the ISF sampling target site.

ISF glucose measurements were made with a modified OneTouch® Ultra® glucose meter and test strip system. A sample of about 1 μL of ISF was extracted from the dermis of the subject's skin layer by a needle and deposited automatically into a measurement zone of the test strip. An unmodified OneTouch® Ultra® glucose meter and strip system was used to determine whole blood glucose values from the finger.

Lag times in minutes and perfusion measurements are given in Table 1 for each subject.

TABLE 1

| Subject ID | control area mean blood perfusion units | treatment area mean blood perfusion units | treatment to control blood perfusion ratio | control ISF overall lag (min.) | treatment ISF overall lag (min.) | overall lag mitigation (min.) |
|---|---|---|---|---|---|---|
| 8 | 97.1 | 212.9 | 2.19 | 30 | 10 | 20 |
| 9 | 65.3 | 170.3 | 2.61 | 21 | 5 | 16 |
| 10 | 84.0 | 187.6 | 2.23 | 26 | 4 | 22 |
| 11 | 50.2 | 117.3 | 2.34 | 22 | −5 | 27 |
| 12 | 68.4 | 223.5 | 3.27 | 12 | −2 | 14 |
| 13 | 95.4 | 295.2 | 3.09 | 30 | 15 | 15 |
| 14 | 62.0 | 150.3 | 2.42 | 47 | 12 | 35 |
| 15 | 51.7 | 92.8 | 1.80 | 50 | 10 | 40 |
| 16 | 80.0 | 80.9 | 1.01 | 41 | 24 | 17 |
| 17 | 64.6 | 107.9 | 1.67 | 46 | 12 | 34 |
| 18 | 101.2 | 244.4 | 2.41 | 50 | 11 | 39 |
| 19 | 86.2 | 142.4 | 1.65 | 27 | 16 | 11 |
| 20 | 114.8 | 256.9 | 2.24 | 42 | 16 | 26 |
| 21 | 118.6 | 198.3 | 1.67 | 13 | 5 | 8 |
| 22 | 73.2 | 156.2 | 2.13 | 25 | 8 | 17 |
| 23 | 114.7 | 278.2 | 2.43 | 30 | 8 | 22 |
| 24 | 94.4 | 253.6 | 2.69 | 15 | 8 | 7 |
| 25 | 161.2 | 482.0 | 2.99 | 8 | −2 | 10 |
| 26 | 58.7 | 151.7 | 2.59 | 42 | 9 | 33 |
| 27 | 114.6 | 363.3 | 3.17 | 29 | 8 | 21 |
| 28 | 56.3 | 117.0 | 2.08 | 31 | 10 | 21 |
| mean: | 86.3 | 203.9 | 2.32 | 30.3 | 8.7 | 1.7 |
| SD: | 28.1 | 97.2 | 0.6 | 12.8 | 6.6 | 9.9 |

The data in Table 1 show that ISF glucose lag was mitigated an average of 21.7 minutes, i.e., from a mean of 30.3 minutes (12.8 SD) to a mean of 8.7 minutes (6.6 SD) by use of the oscillating pressure ring. This lag mitigation was accomplished by the application and release of pressure to the subject's skin layer in a manner that caused an elevation of local blood perfusion in the ISF sampling areas by an average of 2.3 times (0.6 SD) relative to control sampling areas.

While preferred embodiments of the present invention have been shown and described herein, it will be obvious to those skilled in the art that such embodiments are provided by way of example only. Numerous variations, changes, and substitutions will now occur to those skilled in the art without departing from the invention.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An interstitial fluid (ISF) extraction device comprising:
    a penetration member configured for penetrating a target site of a user's skin layer and, subsequently, residing in the user's skin layer and extracting an ISF sample therefrom; and
    at least three concentrically-arranged pressure rings, each of the at least three concentrically-arranged pressure rings adapted for applying pressure to the user's skin layer in the vicinity of the target site while the penetration member is residing in the user's skin layer,
    wherein the ISF extraction device is configured such that the at least three concentrically-arranged pressure rings apply pressure in an oscillating manner with asymmetric deployment and retraction cycle timing, and
    wherein only one of the at least three concentrically-arranged pressure rings is deployed at a time, whereby an ISF glucose lag of the ISF sample extracted by the penetration member is mitigated.

2. The ISF extraction device of claim 1, wherein the ISF extraction device is configured such that the at least three concentrically-arranged pressure rings are capable of applying the pressure in an oscillating manner wherein the pressure is applied for a time period in the range of three seconds to three hours, the pressure is subsequently removed for a time period in the range of three seconds to three hours and then the pressure is re-applied for a period in the range three seconds to three hours.

3. The ISF extraction device of claim 1, wherein the penetration member is configured to reside in the user's skin layer for a period of at least 1 hour.

4. The ISF extraction device of claim 1, wherein the at least three concentrically-arranged pressure rings are configured to apply a pressure in the range of 0.1 to 150 pounds per square inch to a user's skin layer.

5. A method for extracting interstitial fluid (ISF), the method comprising:
  providing an ISF fluid extraction device that includes a penetration member and at least three concentrically-arranged pressure rings;
  contacting the pressure ring with a user's skin layer;
  penetrating the user's skin layer with the penetration member; and
  extracting an ISF sample from the user's skin layer with the penetration member while applying pressure to the user's skin layer in an oscillating manner using the at least three concentrically-arranged pressure rings with asymmetric deployment and retraction cycle timing, and
  wherein only one of the at least three concentrically-arranged pressure rings is deployed at a time and such that an ISF glucose lag of the ISF sample extracted by the penetration member is mitigated.

6. The method of claim 5, wherein the extracting step includes applying pressure in an oscillating manner wherein the pressure is applied for a time period in the range of three seconds to three hours, the pressure is subsequently removed for a time period in the range of three seconds to three hours and then the pressure is re-applied for a period in the range three seconds to three hours.

* * * * *